United States Patent
Frodsham et al.

(10) Patent No.: US 10,265,457 B2
(45) Date of Patent: Apr. 23, 2019

(54) MAGNETIC FILTER APPARATUS AND METHOD

(71) Applicant: MEDISIEVE LTD, Kent (GB)

(72) Inventors: George Charles Martin Frodsham, Kent (GB); Quentin Andrew Pankhurst, Hertfordshire (GB); Richard Alan Wenman, Essex (GB); Simon Richard Hattersley, London (GB)

(73) Assignee: MEDISIEVE LTD, London (GB)

( * ) Notice: Subject to any disclaimer, the term of this patent is extended or adjusted under 35 U.S.C. 154(b) by 175 days.

(21) Appl. No.: 15/264,778

(22) Filed: Sep. 14, 2016

(65) Prior Publication Data

US 2017/0072128 A1    Mar. 16, 2017

Related U.S. Application Data

(60) Provisional application No. 62/218,211, filed on Sep. 14, 2015.

(51) Int. Cl.
*A61M 1/36*    (2006.01)

(52) U.S. Cl.
CPC .......... *A61M 1/3618* (2014.02); *A61M 1/362* (2014.02); *A61M 2206/11* (2013.01)

(58) Field of Classification Search
CPC . A61M 1/3618; A61M 1/362; B03C 2201/18; B03C 2201/26; B03C 1/035; B03C 1/0332; C12M 47/04; B01D 35/06
(Continued)

(56) References Cited

U.S. PATENT DOCUMENTS

| | | |
|---|---|---|
| 3,995,835 A | 12/1976 | Cichy et al. |
| 4,554,088 A | 11/1985 | Whitehead et al. |

(Continued)

FOREIGN PATENT DOCUMENTS

| | | |
|---|---|---|
| WO | 02094351 | 11/2002 |
| WO | 2009097159 | 8/2009 |

OTHER PUBLICATIONS

Bertoni et al., "Nanochains Formation of Superparamagnetic Nanoparticles," J. Phys. Chem. C 2011, 115, 7249-7254.
(Continued)

*Primary Examiner* — Claire A Norris
(74) *Attorney, Agent, or Firm* — K&L Gates LLP

(57) ABSTRACT

A hemofilter system. In one embodiment, the hemofilter system includes a container having a first surface, a second surface, and one or more wall surfaces, the first surface, the second surface and the one or more wall surfaces defining a volume; an input port in fluid communication with the first surface; an output port in fluid communication with the second surface; a filter bed comprising a plurality of planar magnetic meshes stacked in close juxtaposition and positioned within the container volume and coplanar with the first and second surfaces; a first magnet positioned on a first surface of the container; a second magnet positioned on the second surface of the container; a first input conduit in fluid communication with the input port; and a first output conduit in fluid communication with the output port. In another embodiment, the hemofilter system includes a pump in the input conduit.

19 Claims, 15 Drawing Sheets
(1 of 15 Drawing Sheet(s) Filed in Color)

(58) Field of Classification Search
USPC ...... 209/213, 223.1, 232, 214; 210/222, 695
See application file for complete search history.

(56) References Cited

U.S. PATENT DOCUMENTS

| | | | |
|---|---|---|---|
| 5,123,901 | A | 6/1992 | Carew |
| 5,439,586 | A * | 8/1995 | Richards ............. A61M 1/3627 210/222 |
| 5,951,877 | A | 9/1999 | Langley et al. |
| 5,980,479 | A | 11/1999 | Kutushov |
| 6,051,146 | A | 4/2000 | Green et al. |
| 6,071,422 | A | 6/2000 | Hlavinka et al. |
| 6,153,113 | A | 11/2000 | Goodrich et al. |
| 6,231,760 | B1 | 5/2001 | Siddiqi |
| 6,280,622 | B1 | 8/2001 | Goodrich et al. |
| 6,616,623 | B1 | 9/2003 | Kutushov |
| 6,764,859 | B1 | 7/2004 | Kreuwel et al. |
| 7,699,979 | B2 | 4/2010 | Li et al. |
| 8,557,518 | B2 | 10/2013 | Jovanovich et al. |
| 8,768,501 | B2 | 7/2014 | Fischer et al. |
| 8,841,104 | B2 | 9/2014 | Dryga et al. |
| 8,870,446 | B2 | 10/2014 | Rida |
| 8,999,732 | B2 | 4/2015 | Rida |
| 9,150,631 | B2 | 10/2015 | Super et al. |
| 9,156,037 | B2 | 10/2015 | Yung et al. |
| 9,347,595 | B2 | 5/2016 | Toner et al. |
| 9,389,225 | B2 | 7/2016 | Dryga et al. |
| 9,428,547 | B2 | 8/2016 | Dryga et al. |
| 9,593,160 | B2 | 3/2017 | Ingber et al. |
| 9,636,689 | B2 | 5/2017 | Smith et al. |
| 2004/0114458 | A1 | 6/2004 | Berthier et al. |
| 2005/0286342 | A1 | 12/2005 | Garcia et al. |
| 2007/0207272 | A1 | 9/2007 | Puri et al. |
| 2010/0210989 | A1 * | 8/2010 | Macpherson ....... A61M 1/3496 604/6.03 |
| 2010/0331753 | A1 * | 12/2010 | Gandini ............. A61M 1/3621 604/5.02 |
| 2012/0065482 | A1 * | 3/2012 | Robinson ........... A61B 5/14532 600/309 |
| 2013/0217144 | A1 | 8/2013 | Rida |

OTHER PUBLICATIONS

Biswal et al., "Micromixing with Linked Chains of Paramagnetic Particles," Anal. Chem. 2004, 76, 6448-6455.
Calhoun et al., "Paramagnetic particles and mixing in micro-scale flows," Lab Chip, 2006, 6, 247-257.
Correa-Duarte et al., "Alignment of Carbon Nanotubes under Low Magnetic Fields through Attachment of Magnetic Nanoparticles," The Journal of Physical Chemistry B Letters, 2005, 109, 19060-19063.
Fang et al., "Magnetic-field-induced chain-like assembly structures of FE3O4 nanoparticles," EPL, 77 (2007) 68004, 6 pgs.
Frodsham et al., "Biomedical applications of high gradient magnetic separation: progress towards therapeutic haeomofiltration," Biomed Tech (Bert), Oct. 2015;60(5):393-404.
Furst et al., "Micromechanics of Dipolar Chains Using Optical Tweezers," Physical Review Letters, 82 (20):4130-4133, May 17, 1999.
Ganguly et al., "Field-Assisted Self-Assembly of Superparamagnetic Nanoparticles for Biomedical MEMS and BioMEMS Applications," Advances in Applied Mechanics, 41:1-43, 2006.
Häfeli et al., "Optical method for measurement of magnetophoretic mobility of individual magnetic microspheres in defined magnetic field," Journal of Magnetism and Magnetic Materials, 293 (2005) 224-239.
Kang et al., "Chaotic mixing induced by a magnetic chain in a rotating magnetic field," Physical Review E 76, 066303 (2007), 11 pgs.
Kang et al., "Dynamics of magnetic chains in a shear flow under the influence of a uniform magnetic field," Phys. Fluids 24, 042001 (2012).
Ma, et al., "Fabrication of one-dimensional Fe3O4/P(GMA-DVB) nanochains by magnetic-field-induced precipitation polymerization," J. Colloid Interface Sci. (2012), 6 pgs.
Melle, et al., "Chain model of a magnetorheological suspension in a rotating field," Journal of Chemical Physics, 118 (21):9875-9881, Jun. 1, 2003.
Melle et al., "Chain Rotational Dynamics in MR Suspensions," submitted to World Scientific Jan. 24, 2002 : 09:31 P.M., 8 pgs.
Melle et al., "Microstructure evolution in magnetorheological suspensions governed by Mason number," Physical Review E 68, 041503 (2003), 11 pgs.
Petousis et al., "Transient behaviour of magnetic micro-bead chains rotating in a fluid by external fields," Lab Chip, 2007, 7, 1746-1751.
Vuppu et al., "Video Microscopy of Dynamically Aggregated Paramagnetic Particle Chains in an Applied Rotating Magnetic Field," Langmuir, 19(21):8646-8653, 2003.
Wang et al., "Magnetic Nanochains: A Review," NANO: Brief Reports and Reviews, 6(1):1-17 (2011).
Williams et al., "Characterization of magnetic nanoparticles using programmed quadrupole magnetic field-flow fractionation," Phil. Trans. R. Soc. A (2010) 368, 4419-4437.
Wilson et al., "Formation and properties of magnetic chains for 100 nm nanoparticles used in separations of molecules and cells," J. Magn Magn Mater. May 1, 2009; 321(10):1452-1458.
Yung et al., "An Analytic Solution for the Force Between Two Magnetic Dipoles," Magnetic and Electrical Separation, 9:39-52, 1998.
PCT International Search Report and Written Opinion of the International Searching Authority for International Application No. PCT/GB2017/052209, dated Jan. 9, 2018, 14 pages.
PCT International Search Report and Written Opinion of International Searching Authority for International Patent Application No. PCT/EP2016/071719, dated Nov. 29, 2016, 12 pages.

* cited by examiner

TOP PLAN VIEW

PARASITAEMIA REDUCTION BY DEVICE ASSUMING A SEPARATION
EFFICIENCY OF 90% IN A SINGLE PASS, 6% AND 2% INITIAL PARASITAEMIA, AND 5L TBV

MAGNETIC FILTER APPARATUS AND METHOD

RELATED APPLICATIONS

This application claims priority to U.S. Provisional Patent Application No. 62/218,211 filed Sep. 14, 2015, assigned to the assignee of the present application, and whose contents are incorporated by reference in their entirety.

FIELD OF THE INVENTION

The invention relates generally to blood filtering systems and more specifically to magnetic filtering systems.

BACKGROUND OF THE INVENTION

Magnetic separation has been used in mineral processing for years. Generally, it is used to separate out magnetic minerals from mixtures containing non-magnetic materials. In such a separation system, a suspension of particles in a liquid is passed through a magnetisable filter constructed of magnetic wires. Near the wires, a high field gradient results in a magnetic retaining force that attracts any passing magnetisable material.

These magnetic separation techniques can be used with magnetic hemofiltration to remove from the bloodstream anything that is either intrinsically magnetic (i.e., departs significantly from the diamagnetism of normal blood and blood components) or is magnetically labelled with magnetic nanoparticles or beads that target specific blood-borne agents which are available and can be used clinically.

What is needed is a magnetic filter that is capable of extracting magnetically labeled targets in the bloodstream quickly, efficiently and at low cost.

The present invention addresses these requirements.

SUMMARY OF THE INVENTION

One aspect of the invention is a hemofilter system. In one embodiment, the hemofilter system includes a container having a first surface, a second surface, and one or more wall surfaces, the first surface, the second surface and the one or more wall surfaces defining a volume; an input port in fluid communication with the first surface; an output port in fluid communication with the second surface; a filter bed comprising a plurality of planar magnetic meshes stacked in close juxtaposition and positioned within the container volume within the path of fluid from the input port to the output port; a first magnet positioned on a first surface of the container; a first input conduit in fluid communication with the input port; and a first output conduit in fluid communication with the output port wherein the first magnet produces a magnetic field that is modified by the presence of the planar magnetic meshes in such a way as to produce a sufficiently strong and inhomogeneous magnetic field in the free space within the filter bed to allow the capture of blood-borne magnetic targets. In another embodiment, a second magnet is positioned on a second surface of the container.

In yet another embodiment, the hemofilter system includes a pump in the input conduit. In still another embodiment, the hemofilter system includes a saline drip unit in fluid communication with the input conduit. In yet another embodiment, the hemofilter system includes a saline reservoir and a syringe pump connected in parallel fluid communication with the first conduit through a T-junction.

In still yet another embodiment, the hemofilter system includes an air detector in fluid communication with the output conduit. In one embodiment, the hemofilter system includes a pressure detector in fluid communication with the output conduit.

In another aspect, the invention is a hemofilter including a container having a first surface, a second surface, and one or more wall surfaces, the first surface, the second surface and the one or more wall surfaces defining a volume; an input port in fluid communication with the first surface; an output port in fluid communication with the second surface; a filter bed comprising a plurality of planar magnetic meshes stacked in close juxtaposition and positioned within the container volume and coplanar with the first and second surfaces; a first magnet positioned on a first surface of the container; a second magnet is positioned on a second surface of the container; wherein the first and second magnets produce a magnetic field that is perpendicular to the planar magnetic meshes and which produces a sufficiently strong and inhomogeneous magnetic field in the free space within the filter bed to allow the capture of blood-borne magnetic targets.

In yet another embodiment, the filter is designed to produce a uniform flow characteristic at a millimeter-scale length so as to avoid dead-spots and eddies, and to maintain a sufficient rate of flow overall by producing a labyrinthine flow pathway for each individual red blood cell that passes through the filter. In one embodiment, the flow causes a red blood cell to deviate from its unimpeded flow by more than three times the diameter of the red blood cell. In another embodiment, the deviation from unimpeded flow is by more than about 20 microns.

In general, the hemofilter is designed to produce a three-dimensional, braided, laminar flow on the part of the blood that passes through the filter. In this aspect, the flow of the blood is like that of a meandering riverbed, but through a three-dimensional volume rather than over a two-dimensional surface. In one embodiment, the stack of planar metal-wire meshes are arranged in such a way that the blood passing through the filter separates into a series of laminar flow channels that serially divide and recombine as they move through each layer of mesh. The laminarity of the flow is retained throughout the entirety of the mesh-stack-filled portion of the filter, so that at no time during the passage of the blood is it subjected to any violent or potentially damaging turbulent motion. At the same time, the serial division and recombination of the laminar flow channels ensures that each and every fraction of the blood—such as for example a given individual red blood cell or magnetically-labeled biomolecule—has a finite, greater-than-zero probability of physically encountering at least one capture site (defined as being the volume of space sufficiently close to the magnetically actuating mesh that, for a magnetic or magnetically labeled entity of the anticipated magnetic character, moving at the anticipated speed, the entity will be captured (retained and held) as it transits the mesh-stack-filled portion of the filter.

In one embodiment, the multi-layer stack of wire meshes is arranged in such a way that the laminar flow channels that the blood separates into as it passes through the mesh-stack-filled portion of the filter is highly regularized, so that the three-dimensional pattern of flow channel division and recombination would take on a regular, well-defined structure. Such an embodiment is achieved by having the mesh layers arranged in space in a repeated, sequential, and aligned fashion.

In another embodiment of this aspect of the hemofilter, the multi-layer stack of wire meshes is arranged in such a way that the laminar flow channels that the blood separates into as it passes through the mesh-stack-filled portion of the filter are more random, stochastic or convoluted, so that the three-dimensional pattern of flow channel division and recombination would take on an irregular, random structure. Such an embodiment is achieved by having the mesh layers arranged in space in a non-aligned, random fashion.

In a further aspect, the hemofilter is designed in such a way that the Reynolds number of the blood passing through the mesh-stack-filled region of the filter is typical of that of a laminar, rather than turbulent, or transitional (meaning intermediate between laminar and turbulent) flow. The Reynolds number can be defined in several ways, two of which are described here for illustrative purposes, and the operator should apply the appropriate definition to the embodiment of hemofilter used. In the first case, the Reynolds number is defined as $Re=\rho v L/\mu$, where $\rho$ is the density of blood (ca. $1.06\times10^3$ kg m$^{-3}$), v is the mean velocity of the blood as it passes through the filter, L is a characteristic dimension of the filter such as the mesh aperture size, and $\mu$ is the viscosity of blood (ca. $3\text{-}4\times10^{-3}$ Pa s). In this case, Re is less than or of order 2300 for laminar flow. In the second case, the Reynolds number is that which is defined for randomly packed beds of hard spheres, $Re^*=\rho u\, d/\mu(1-\varepsilon)$, where $\rho$ and $\mu$ are defined as before, u is the superficial flow rate of the blood through the filter (given by the volumetric flow rate through the filter divided by the macroscopic cross-sectional area of the filter), d is the spherical equivalent particle diameter (i.e. the diameter of the spheres that would occupy the same volume of space as that occupied by the given filter mesh material), and $\varepsilon$ is the bed voidage (meaning the volumetric fraction of the filter that is not occupied by the filter material). In this case, $Re^*$ is less than or of order 10 for laminar flow.

In a yet further aspect, the hemofilter is designed to provide efficient capture at flow rates and at filter volumes commensurate with both the rate of flow of blood to and from a human artery or vein, and acceptable safety limits on the amount of blood that can be held extracorporeally at any given time. For children, this corresponds to flow rates from 40 to 200 ml/min, and extracorporeal volumes of order 8% of the total blood volume—which for example in a 5 year old child weighing 20 kg would be of order 0.08×1.6 liters=128 ml. In adults, this corresponds to flow rates from 40 to 400 ml/min, and extracorporeal volumes of order 8% of the total blood volume–which for example in an 80 kg adult would be of order 0.08×6.4 liters =512 ml.

In a still further aspect, the hemofilter is designed to contain quiescent capture zones for the retention and safe collection of fragile or delicate biological entities. This aspect requires that the capture zones be intrinsically active with respect to flow—as otherwise they would constitute 'dead zones' through which the blood would not pass—while also being suitable as receptacles of the targeted and captured biological entities. In one embodiment, these quiescent capture zones are located along the lengths of opposite sides of wires magnetized perpendicularly to the orientation of the wire and parallel to the direction of flow, creating areas of high magnetic force and low drag force, facilitating capture.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

DESCRIPTION OF A PREFERRED EMBODIMENT

Figure 1:
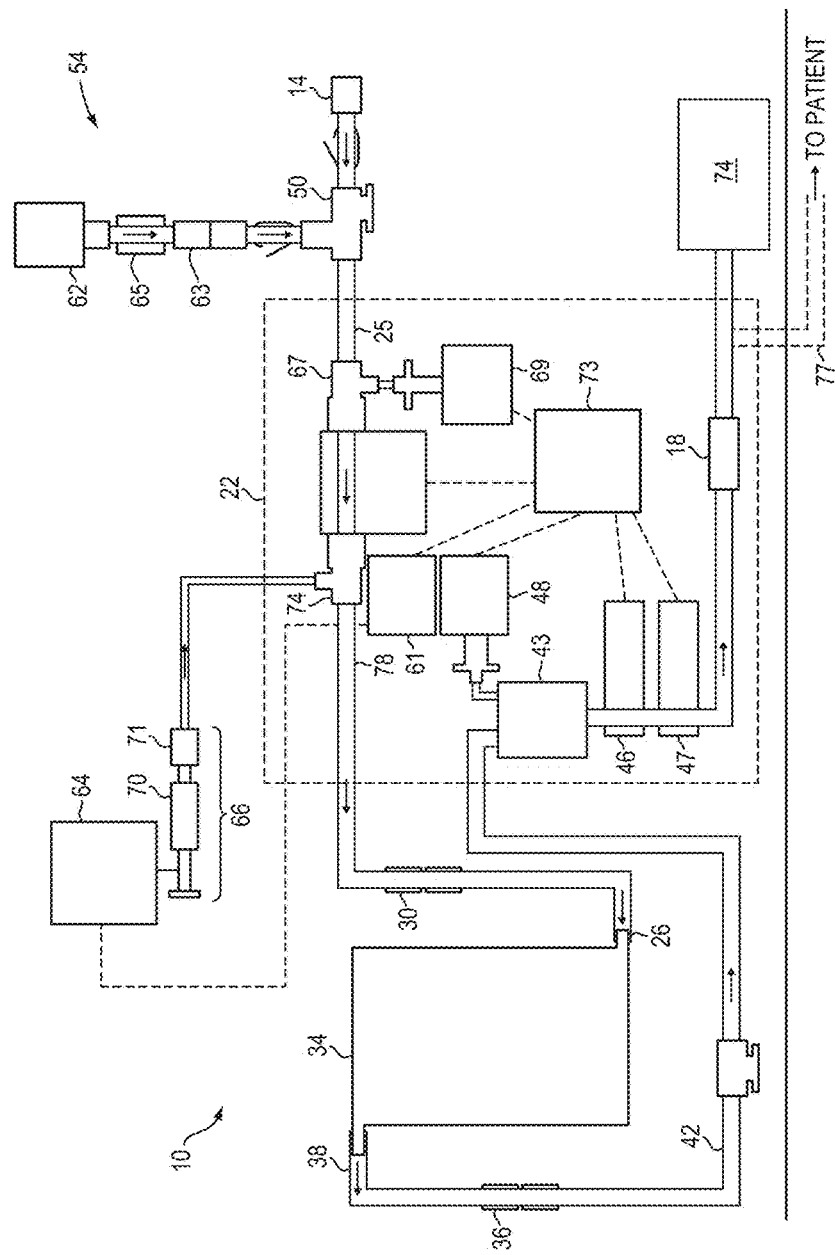
FIG. 1 is a block diagram of an embodiment of the system of the invention.
Figure 2:
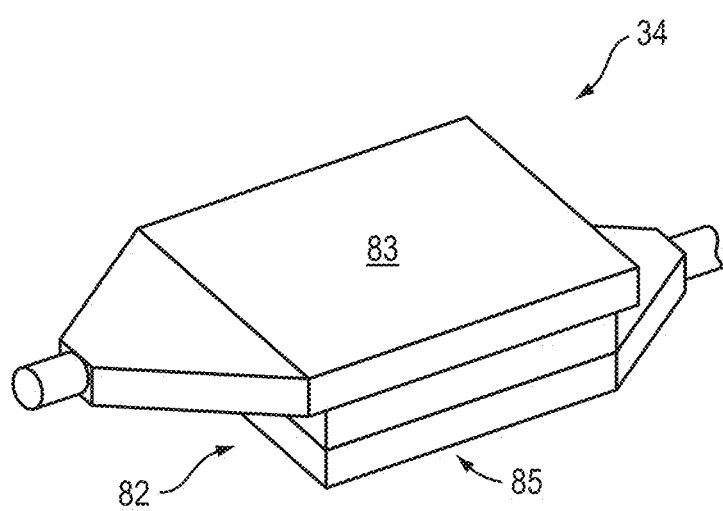
FIG. 2 is a perspective diagram of the magnetic filter housing.

Referring to FIG. 1, a system 10 constructed in accordance with an embodiment of the invention includes an input port 14 and an output port 18. In one embodiment, the input 14 and output 18 ports include Luer-type connectors configured to engage the corresponding mating Luer-type connector of a patient's catheter. Blood from the patient is drawn into the system 10 through the input port 14 with a pump 22 connected to an input conduit 25. In one embodiment, the pump is a peristaltic pump. The other end of the input line also includes a Luer-type connector 30 positioned to engage a corresponding mating Luer-type connector 32 configured as the input port 26 of a magnetic filter 34.

A Luer-type connector of the output port 38 of the magnetic filter 34 engages a Luer-type connector 36 at one end of the system output conduit 42. The other end of the system output conduit 42 includes a Luer-type connector that acts as the system output port 18. The Luer-type output port engages a catheter that returns blood to the patient. In one embodiment, the peristaltic pump 22 is an infusion pump, (Baxter International, Deerfield, Ill., infusion pump model BM-11) and includes an output circuit that includes a gas trap with filter 43 and an air detector 46 to detect and/or filter air bubbles in the blood flow (arrows). In this embodiment, the peristaltic pump includes a pressure sensor 48 in the output circuit to assure that the pressure of the blood flowing back into the patient is within the desired limits. Also in this embodiment the output circuit includes an emergency clamp 47 that can stop flow through the circuit if bubbles are detected. In various embodiments, the input 25 and output conduits 42 are constructed of air-permeable tubing. In one embodiment, the output conduit 42 is attached to a collection receptacle 74. In another embodiment, the output conduit 42 is connected to a cannula 77 to return a patient's blood to the patient.

In one embodiment, a controller 73 controls the syringe pump 64 through a digital port 61 and the peristaltic pump 22.

In another embodiment, a saline drip subsystem 54 is connected through Luer connectors 63 to the input line 25 through a first T-connector 50. In one embodiment, the saline drip subsystem 54 includes a saline reservoir drip bag 62 having a manual IV line control valve 65. The input line 26 is connected to the input of a peristaltic pump 22 through a second T-connector 67. A second port of the second T-connector 67 is connected to an input pressure sensor 69 to measure the fluid pressure at the input line 25 prior to the pump 22.

The output of the peristaltic pump 22 is connected to a syringe pump 64 having a syringe pump driver 66 controlling the flow of an anticoagulant, such as heparin, from a syringe 70 through a third T-connector 74. The output 78 of this third T-connector 74 is a second input to the input conduit 26. This anti-coagulant subsystem assures that no clotting of the patient's blood occurs as it passes through the system 10.

In more detail, and referring to FIGS. 2 and 3A-D, the magnetic filter 34 includes an outer container 82. In one embodiment, the outer container 82 is made of a disposable plastic or a sterilizable material. In one embodiment, the plastic is a medical-grade plastic such as a polyethylene, polycarbonate or silicone. In one embodiment, the inner surfaces of the container and the mesh are coated with an anticoagulant. In one embodiment, the anticoagulant coating is a composite polysaccharide with embedded heparin. The outer container 82 is typically permanently sealed by top 83 and bottom 85 lids but may be configured to be opened for cleaning and refurbishment. The size of the container housing 82 is determined in part by the size of the patient to whom the system is to be connected. If the volume of the filter 34 is too large, the patient will experience a reaction due to excess blood loss. If the volume is too small, the amount of time needed to move a significant fraction of the patient's blood through the device becomes excessive.

Generally, in nephrology, the maximum amount of blood to be withdrawn from a patient in an extracorporeal loop is 8% of the patient's blood volume. The average adult has about five liters of blood so the amount of blood in the extracorporeal circuit should be less than about 400 ml. Reducing this further by 50% to account for the fact that some of the patients will be anemic, the volume of the extracorporeal circuit becomes about 200 ml. This volume must be reduced for children. For an infant under 12 months of age the volume of the system is about 30 ml. The tubing and connectors of the system are assumed to contain about 10 ml of blood and that means that the housing volume will vary from about 20 ml for infants to about 190 ml for an adult.

Because the outer container 82 includes a magnetic metal mesh filter that occupies up to one third of the volume of the container, the actual container volumes are about one third greater than the desired blood volume. Thus, a chamber sized for an adult (about 190 ml of blood) is about 250 ml in volume.

The shape of the container is designed to increase flow rate through the container by reducing the drag force. To reduce the drag force, the container is constructed to have one pair of surfaces, for example top and bottom, with a larger surface area compared to the other (in this embodiment, four) surfaces of the container. Note that in this discussion the filter is discussed, without the loss of generality, as a rectangular parallelepiped but other shapes including cylindrical are contemplated. In one embodiment, the flow of blood is then oriented perpendicularly between the two larger surfaces. For example, if a volume of 125 ml is desired, rather than constructing the container to have each edge of the six surfaces being 5 cm (5×5×5 cm), it is advantageous to have dimensions of 12.5×10×1 cm, so that the top and bottom surfaces are 125 cm$^2$. In the first case (5 cm for each edge of each surface), the largest surface area is 25 cm$^2$. In the second example, the area of the largest surfaces (top and bottom) is 125 cm$^2$. Since the linear flow velocity of a liquid for a given volumetric flow rate depends on the area of the surface through which the liquid flows, maximizing the surface area minimizes the linear flow velocity, and thus the drag force. Thus, the drag would be reduced by a factor of five for flow between the two largest surfaces. It is important to note however, that increasing one side at the expense of the others will reduce the height of the filter bed.

To make use of the increased surface area, it is necessary to divert the input blood flow so that it spreads out over the larger surface. Referring again to FIG. 3A-D, the input port 26 of the container provides blood flow through a flow homogenizer or disperser 80. As the blood passes down the tube 80 (FIG. 3C), the tube becomes wider and flatter causing the blood to spread over the surface as the volume fills, eventually reaching the output port 38. In some embodiments, the blood flows through a flow homogenizer or diverter before exiting at output port 38 in order to maintain flow homogeneity at the top of the chamber. Other forms of diverters or homogenizers are possible. It should be noted that although this system is generally described with the input port 26 at the bottom and the output port 38 at the top, the orientation of the container is not relevant, although if the volume of blood flow is between the two largest surfaces, efficiency is increased.

Figure 3A:
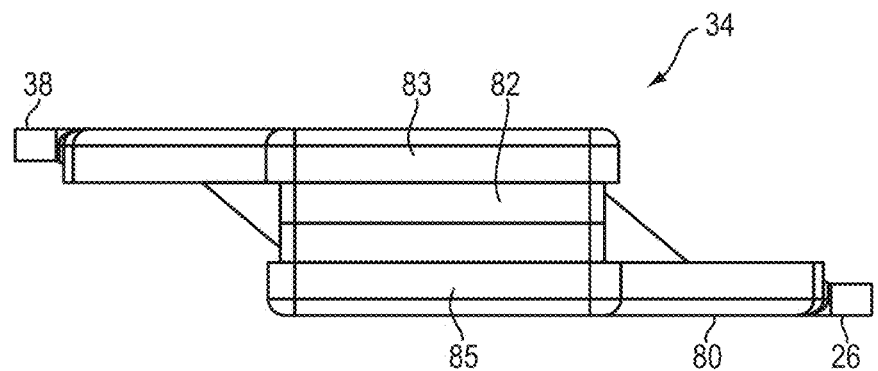
FIG. 3A is a side view of the embodiment of the magnetic filter housing shown in FIG. 2.
Figure 3B:
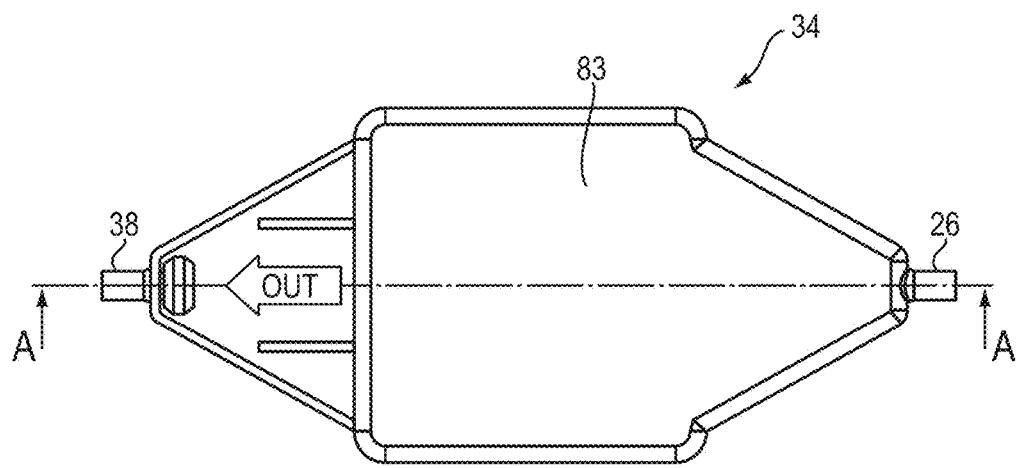
FIG. 3B is a bottom view of the embodiment of the magnetic filter housing shown in FIG. 2.
Figure 3C:
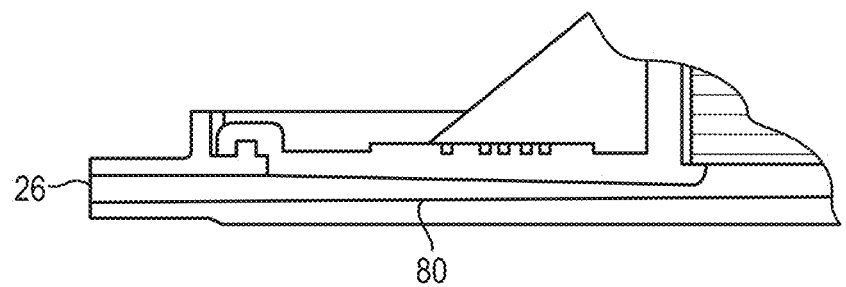
FIG. 3C is a cross-sectional view of a flow homogenizer of the embodiment of the magnetic filter housing shown in FIG. 2.
Figure 3D:
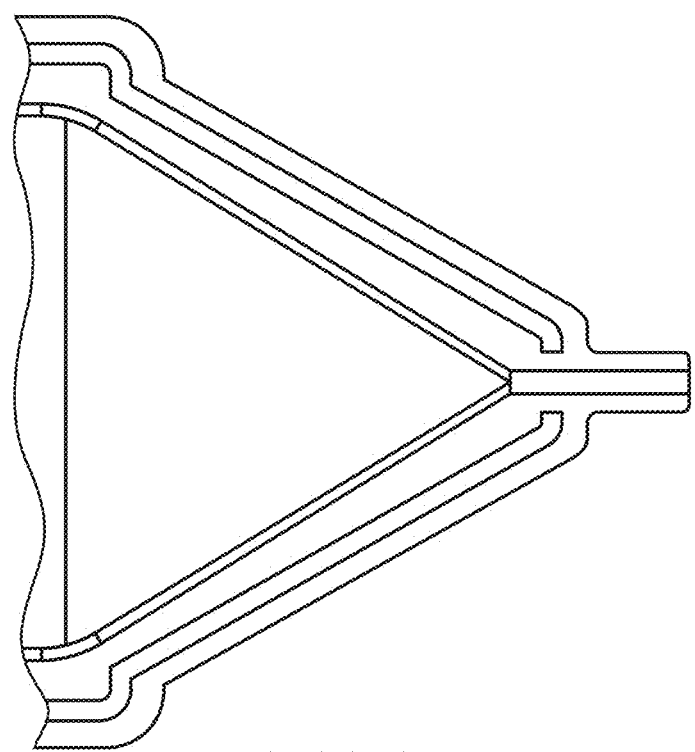
FIG. 3D is a top plan view of a flow homogenizer of the embodiment of the magnetic filter housing shown in FIG. 3C.
Figure 4A:
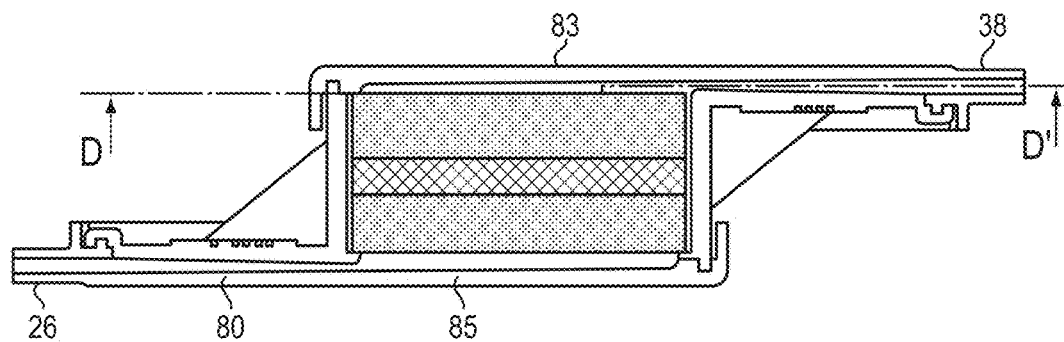
FIG. 4A is a cut away view of the embodiment of the magnetic filter housing shown in FIG. 2.
Figure 4B:
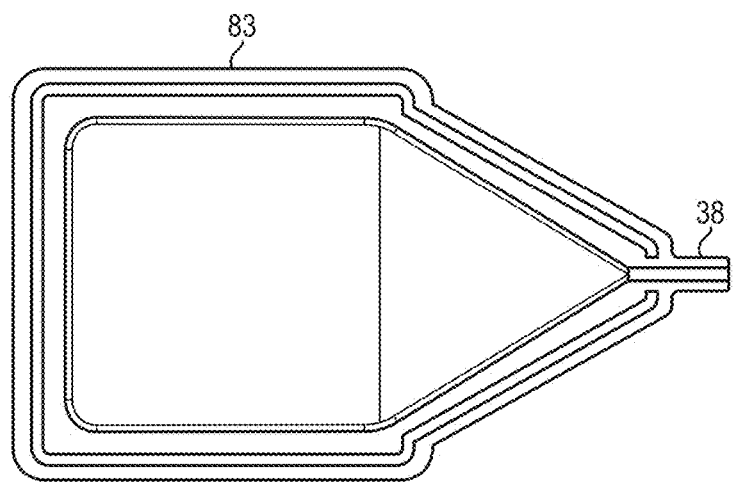
FIG. 4B is a top cut away view of the embodiment of the magnetic filter housing shown in FIG. 4A through line DD'.

One issue with a container having orthogonal walls is that the corners where the walls meet form "dead spaces" where fluid collects and does not flow with the majority flow through the container. These dead spaces in some embodiments are removed by forming continuous non-orthogonal surfaces where the walls of the corner of a container meet (FIG. 3B). In one embodiment, the inner surfaces of the container are coated with a hydrophobic coating. In one embodiment, the hydrophobic coating is a silicone based polymer such as polydimethylsiloxane.

Figure 5A:
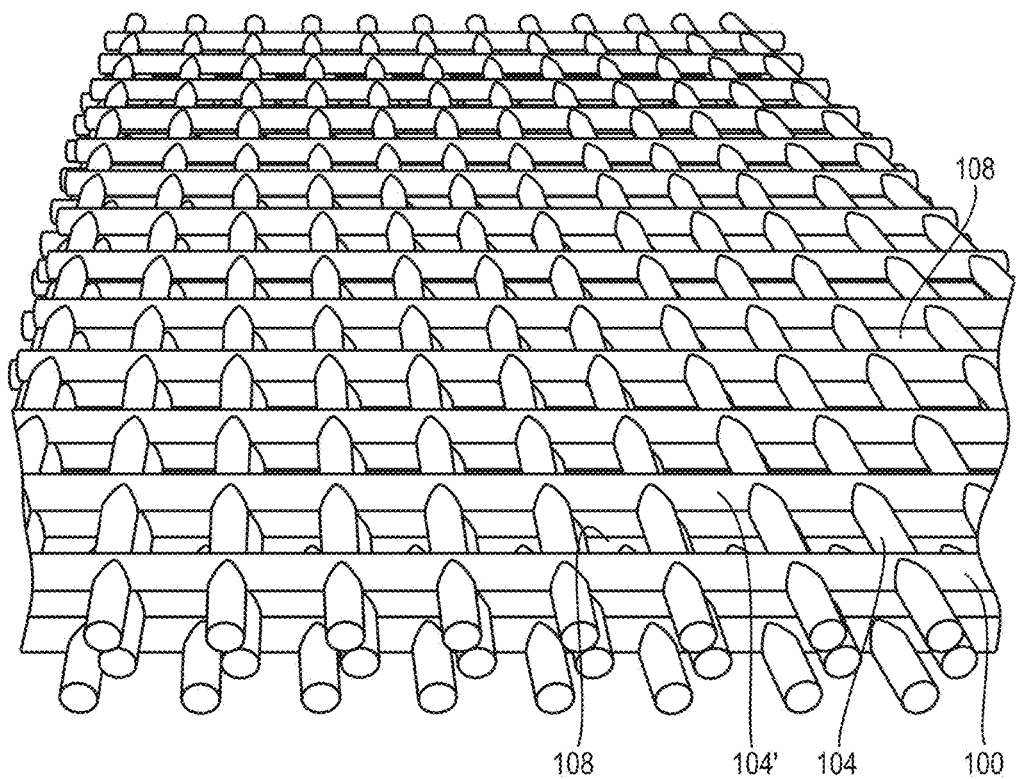
FIG. 5A is a perspective diagram of an embodiment of the mesh layers of a five layer magnetic mesh filter.
Figure 5C:
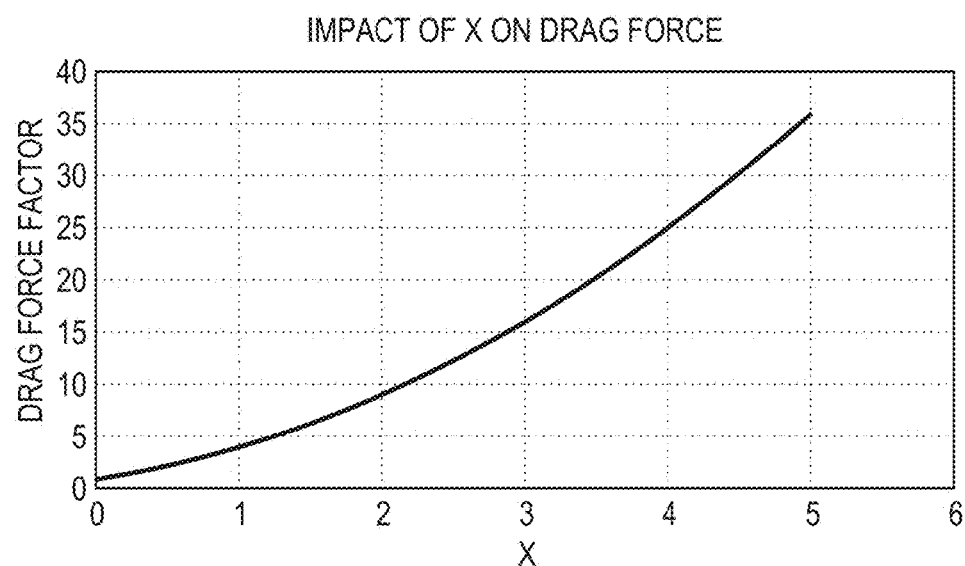
FIG. 5C is a graph of the effect on the drag force on fluid flow of the ratio of the wire diameter to the length of the side of the aperture.
Figure 5B:
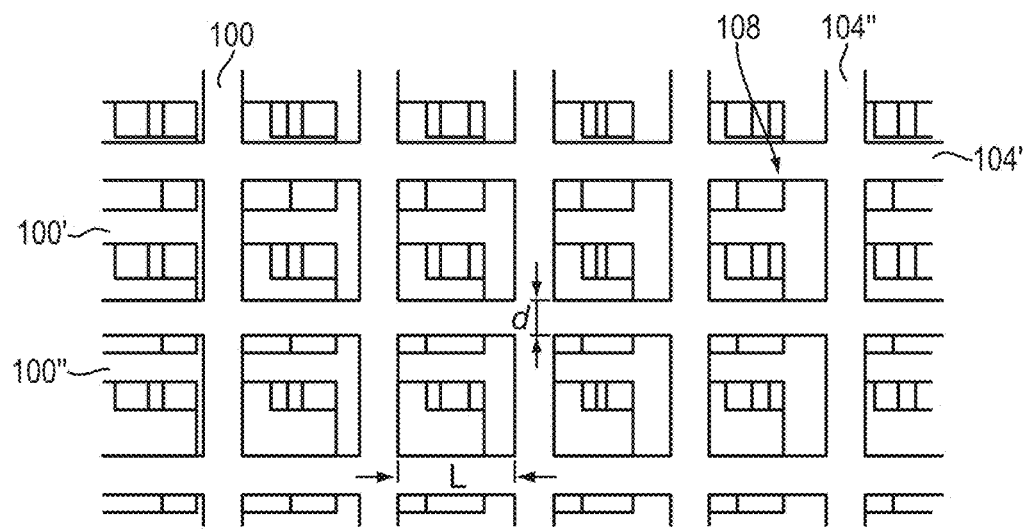
FIG. 5B is a plan view of a portion of the five layer filter of FIG. 5A, magnified to show the staggered arrangement of the wires.

Referring to FIGS. 5A, B, within the container 82 is a filter bed through which the blood entering the container 82 passes as it flows to the output port 38. In one embodiment, the filter bed is constructed as a plurality of planar meshes 100, 100' . . . 100", (generally 100) stacked together. In one embodiment, the plane of the mesh is preferably perpendicular to the flow of blood through the container volume. The mesh is constructed of non-diamagnetic (including, but not limited to, ferro or ferri strands) wires 104' . . . 104" (generally 104) woven to an aperture spacing (generally 108) of 10-1000 microns and preferably of 50 microns between the wires. In one embodiment, the non-diamagnetic wires are SS430 stainless steel, with a wire diameter of 10-1000 microns and preferably 250 microns. In one embodiment, such a configuration of at least one hundred layers of mesh corresponds to approximately thirty mm in thickness. The meshes 100 are stacked, each mesh randomly offset from the previous layer such that the spacings between the wires of each mesh are staggered to form interrupted channels through the filter bed (FIG. 5B). A blood cell flowing through the filter bed therefore has a high probability of encountering multiple wires as it flows up the channel. As a result of the higher magnetic fields in the free space adjacent to the wires, as described below, magnetic or magnetically labeled components within the flow of blood experiences a magnetic retarding force component slowing the flow. FIG. 5C is a graph of the effect on the drag force of the ratio of the wire diameter to the length of the side of the aperture. That is, as the wire diameter becomes larger relative to the side of the aperture, the drag force increases rapidly due to the decrease in aperture size.

Figure 6A:
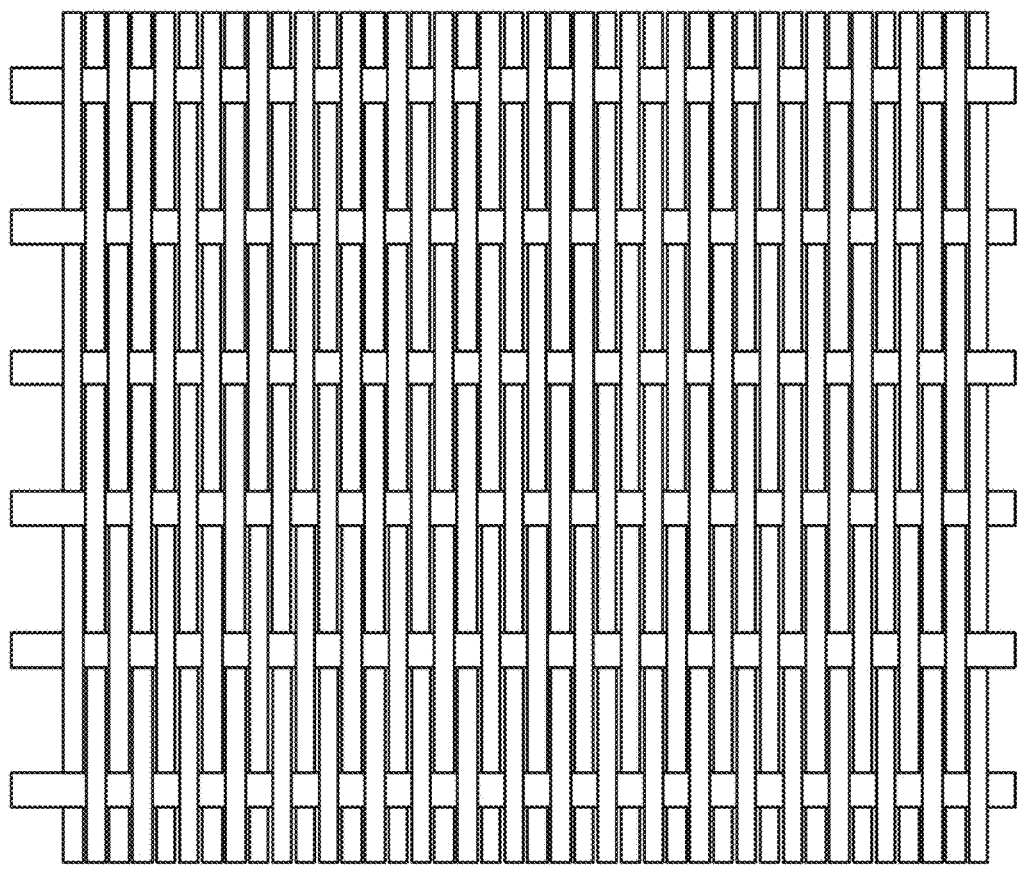
FIG. 6A is a plan view of an embodiment of the mesh of a magnetic filter in Dutch weave configuration.
Figure 6B:
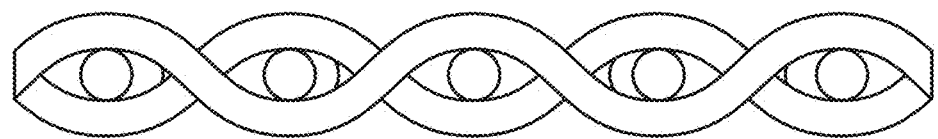
FIG. 6B is a side view of an embodiment of the mesh of a magnetic filter in a plain Dutch weave configuration.
Figure 6C:
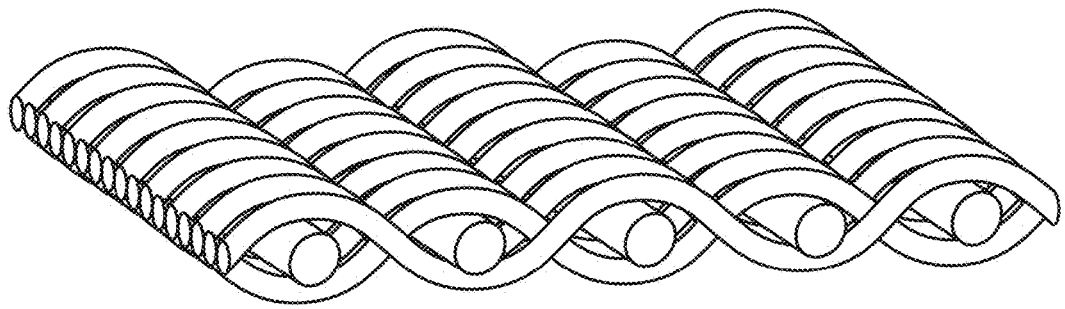
FIG. 6C is a perspective view of the embodiment of the mesh of the magnetic filter of FIG. 6B.
Figure 6D:
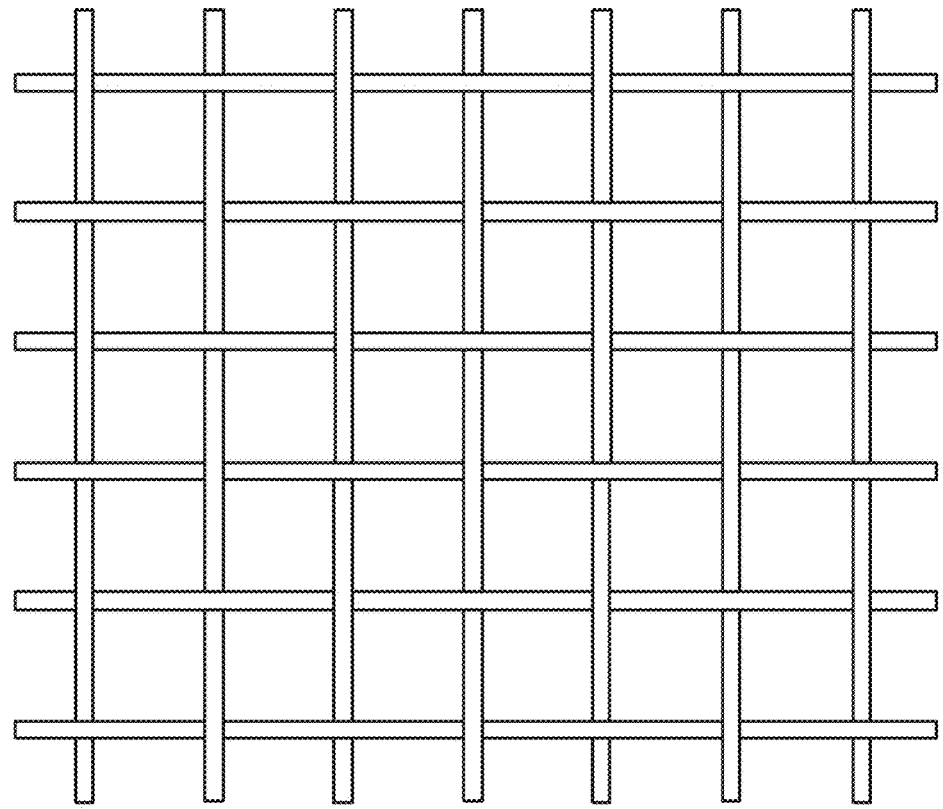
FIG. 6D is a plan view of the embodiment of the mesh of the magnetic filter in a plain or one over another weave configuration.
Figure 6E:
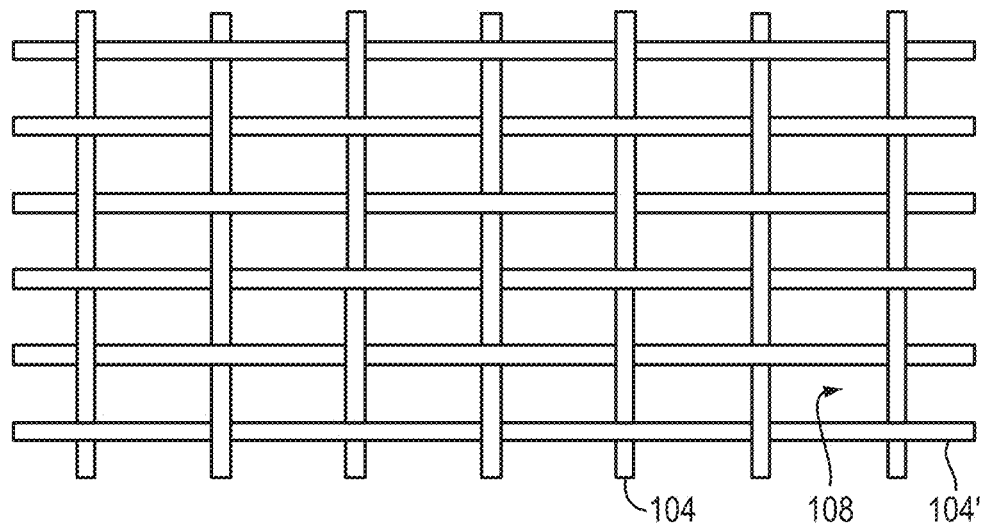
FIG. 6E is a plan view of the embodiment of the mesh of the magnetic filter in a plain or one over another weave configuration in which the spacing between the wires in each direction is different.
Figure 6F:
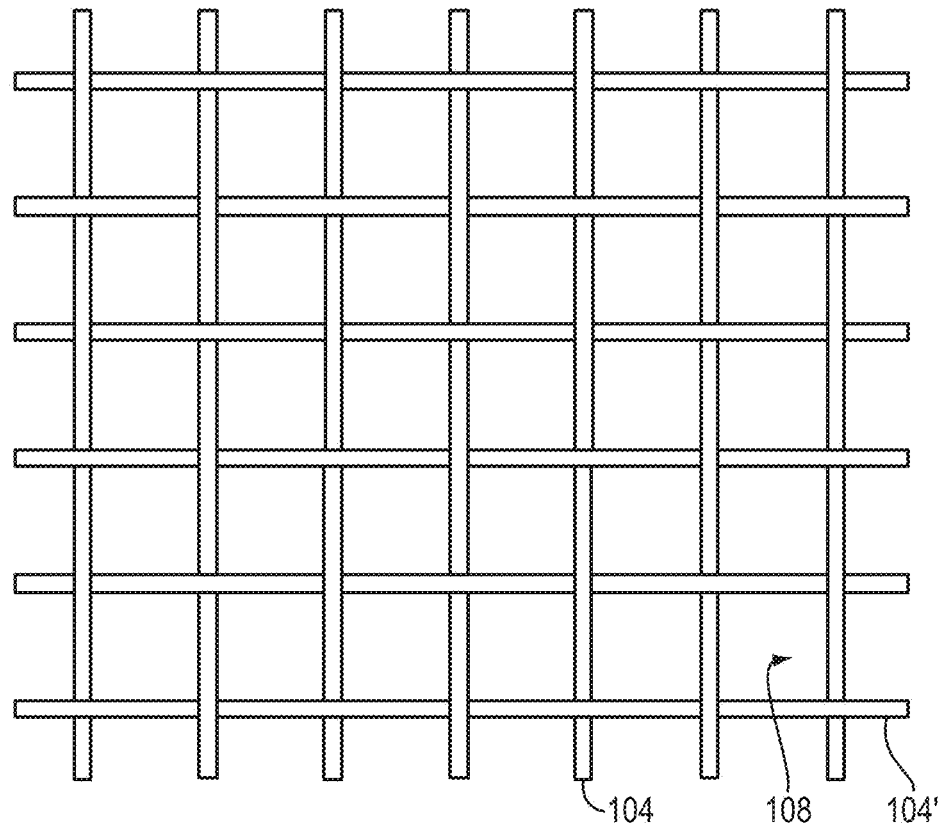
FIG. 6F is a plan view of an embodiment of the mesh of a magnetic filter in twill or two over two under weave configuration.

Referring to FIGS. 6A-F, the magnetic mesh filters may take on many forms or weaves; several embodiments are herein discussed. FIG. 6A is an embodiment of a magnetic mesh filter in a Dutch weave configuration. In Dutch weave, the "warp" and "weft" wires have different diameters. FIG. 6B is a side view of an embodiment of a magnetic filter mesh in a Dutch weave configuration, FIG. 6C is a perspective plan view of the same magnetic filter mesh of FIG. 6B. FIG. 6D is a plan view of a magnetic filter mesh in a plain or one over another weave configuration. FIG. 6E is an embodiment of the mesh of the magnetic filter of FIG. 6D in which the spacing between the wires in each direction is different. FIG. 6F is an embodiment of the mesh of a magnetic filter in twill weave configuration. In general, the weaves are chosen such that areas of substantially maximum magnetic retarding forces overlap with the areas of substantially minimum viscoelastic drag forces as discussed below.

Figure 7:
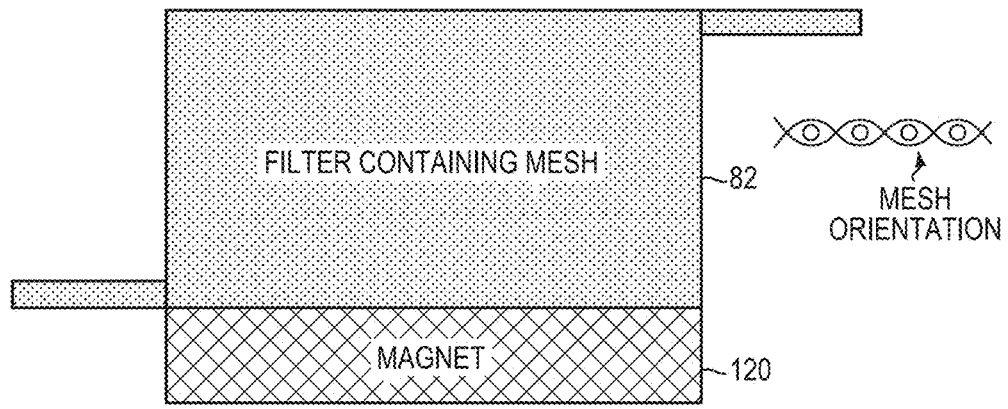
FIG. 7 is a block diagram showing an embodiment of a filter housing positioned adjacent a magnet.
Figure 8:
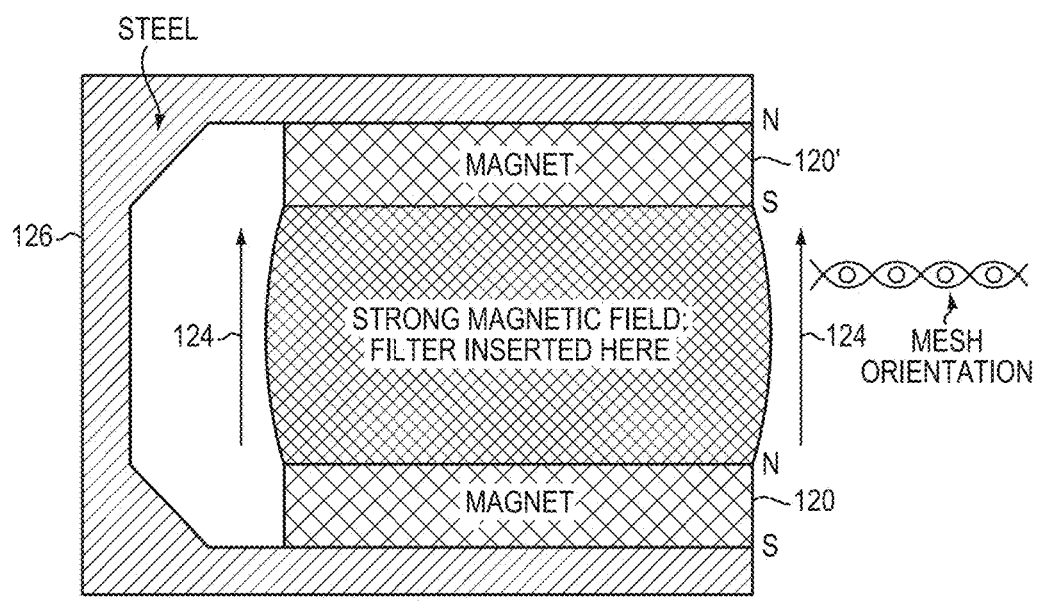
FIG. 8 is block diagram of an embodiment of a two magnet assembly with a steel keeper.

Referring to FIG. 7, to establish the appropriate magnetic field in the mesh, in one embodiment, the container 82 containing the mesh filter is placed adjacent a permanent magnet 120. In a second embodiment FIG. 8, to increase the magnetic field, two permanent magnets 120, 120' orientated with the same polarity are applied to the opposite sides of the container 82 such that the magnetic field 124 is perpendicular to the planes of the meshes 100. This embodiment includes a keeper 126 to provide a return path for the magnetic field.

Figure 9:
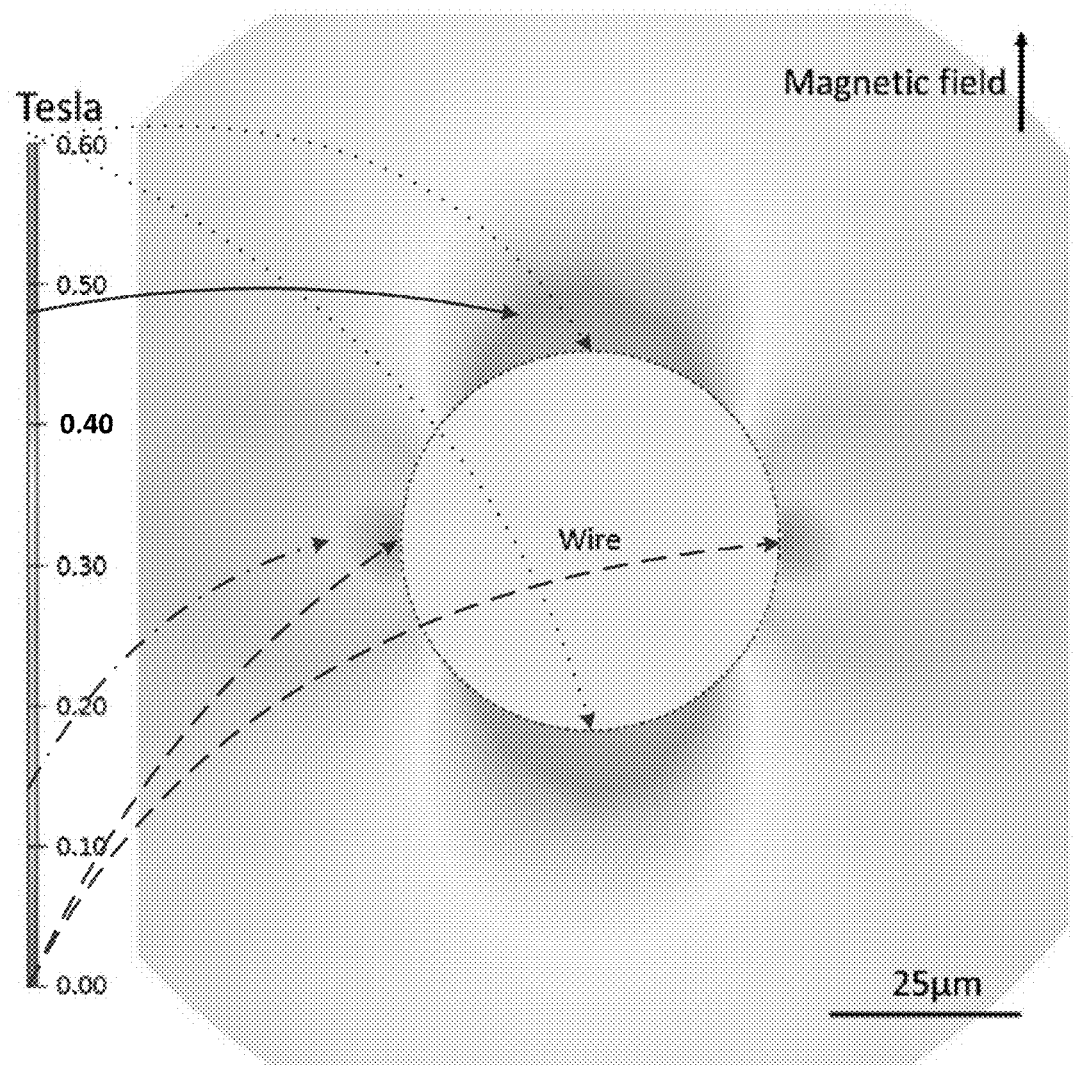
FIG. 9 is a field diagram of a magnetic field adjacent a cylindrical wire whose cylindrical axis is perpendicular to the external applied field.

Such a configuration induces an approximately equal magnetic field acting on each of the wires 100 and 104 forming each aperture 108 in the mesh. However, given that the mesh is made from a ferromagnetic or ferrimagnetic material that is intrinsically magnetizable (leading to an induced magnetization within the wires), the magnetic field acting within each aperture 108 in the mesh is modified to become the superposition of the field due to the permanent magnets 120 and 120' and the magnetic field generated by the magnetized wires 100, 100', 100" etc. and 104, 104', 104" etc. The field due to the magnetized wires is approximately that of a magnetic dipole, and is therefore maximal in the direction of the magnetizing field, and falls off rapidly (scaling as $1/r^3$ where r is distance from the wire) along the direction of the magnetizing field (FIG. 9). A color coded legend is shown on the left side of the figure such that colors are used to represent magnetic field strength ranging from about 0 Tesla (dark blue) to about 0.60 Tesla (dark pink).

Figure 10:
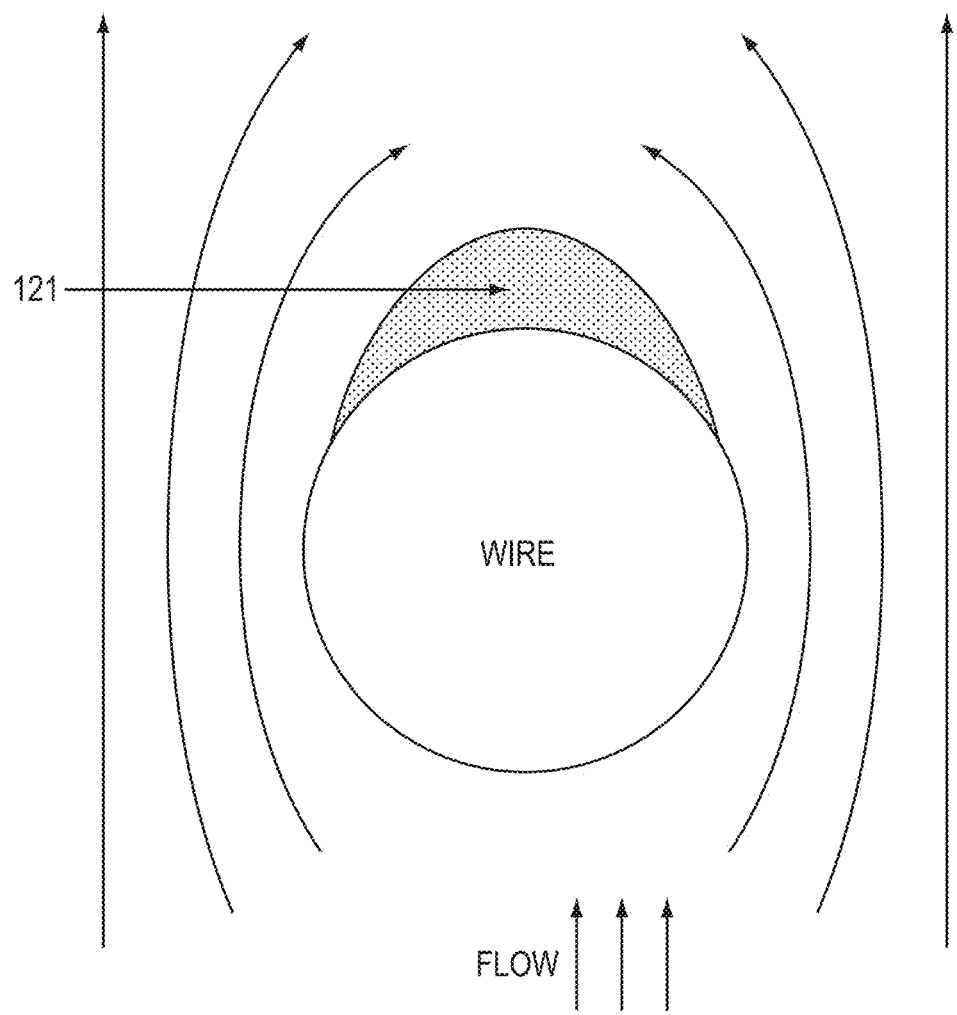
FIG. 10 shows a quiescent capture zone adjacent a wire in a magnetic field.

Still referring to FIG. 9, a first pair of dotted arrows extends from the top of the figure legend on the left and point to the high field values (about 0.6 Tesla, dark pink) in the direction of the magnetic field as shown near the top and bottom of the cross-section of the wire. A second pair of arrows extends from the bottom of the legend and point to the low field values (approaching zero, dark blue) on the left and right sides of the wire cross-section. A solid arrow and another dotted arrow are also included to emphasize two additional points (about 0.15 Tesla and about 0.48 Tesla) in the field to give further context to the legend. The summed magnetic field is therefore strongest, and has the highest field gradients in the near vicinity of each wire. If a fluid containing magnetic targets is then passed through the filter mesh in such a way that the flow direction is parallel to the direction of the magnetizing field, then, as shown in FIG. 10, a region of maximal magnetic trapping is created adjacent each of the wires of the mesh, that region being characterized as one with a combination of relatively large magnetic retarding forces and relatively small viscoelastic drag forces.

The magnetic force ($F_m$) experienced by a magnetic particle passing near the wires of the mesh is given by the expression:

$$F_m = \mu_o \chi V H \nabla H$$

where $\mu_0$ is the permeability of free space, $\chi$ is the volumetric magnetic susceptibility of the magnetic material, V is the volume of magnetic material in the particle, H is the magnetic field adjacent the wire ($\chi V H$ being the total magnetic moment, M, of the particle), $\nabla H$ is the magnetic field gradient near each wire, and bolding indicates a vector. Close to the wires of the mesh, the magnetic field gradient becomes large.

Similarly, the drag force ($F_d$) applied a spherical object in a liquid flow is described by Stokes' law, and is a good approximation for the drag force felt by the magnetized and/or magnetizable entities the filter is to capture:

$$F_d = 6\pi\mu R v$$

where μ is the liquid viscosity, R is the radius of the cell, and v is the velocity of the liquid relative to the cell. The velocity v of the liquid exerting a force on a particle is dependent on the volumetric flow rate, f (ml/min) and the cross-sectional flow area C, and is given by the expression:

$$v = \frac{f}{C}$$

Because the filter chamber cross-sectional area is reduced by the amount of space taken up by the wires of the mesh, the actual cross-sectional area of the filter is reduced and therefore the liquid flow velocity, and hence also the drag force $F_d$ is dependent on γ, the fractional change in area, which in turn is dependent on x, the ratio between d, the diameter of each wire, and l, the length of one side of an aperture in the mesh, $$x = \frac{d}{l}$$
$$\gamma = \frac{1}{1+x}$$

If the diameter of the wire is ⅕ of the length of the aperture side, the cross-sectional area of the filter decreases to 70% and the flow rate is decreased to 44%. The effect of the ratio x on the drag force is shown in FIG. 5C.

For capture to occur, the drag force $F_d$ must be less than the magnetic force $F_m$. To assure this relationship is met, the following options may be used in the design and deployment of the device. The magnetic force may be increased by increasing the magnetic field H by varying the type and configuration of permanent magnets or electromagnets creating the external field (as discussed below). Alternatively, the field gradient ∇H may be varied or optimized by: optimizing the magnitude of H for the particular dimensions and magnetic properties of the wires; using a ferromagnetic mesh with a higher magnetic susceptibility or higher magnetic saturation; or optimizing the diameter of the wire consistent with the magnetic field. The capture of a specific target such as a magnetic particle can be improved by increasing the magnetic moment of the magnetic particle either by increasing the volume of magnetic material of the target or by using a material with higher magnetic susceptibility.

Further, one could increase the likelihood of a target passing through an area of high field gradient. In the case of a target flowing through the aperture of a mesh, the magnetic force is lowest in the center of the aperture. The use of a randomized stacked mesh design, with a large number of layers, ensures that targets have a very low probability of never passing through areas of high gradient (i.e. close to the surface of a wire). Further decreasing the drag force may also be accomplished by: lowering the velocity of the targets (this may be undesirable since it would increase the overall treatment time); increasing the cross-sectional flow area (which also may be undesirable as it is limited by the total volume of blood that can be removed from a patient in an extra-corporeal loop (typically 8% of TBV); or using a mesh with a higher aperture size-to-wire diameter ratio (i.e., lower x). This last option must be balanced with ensuring the apertures are small enough that sufficient targets pass close to the wires, because large apertures may create flow paths through the channels in which a particle never enters an area of high magnetic gradient.

Figure 11:
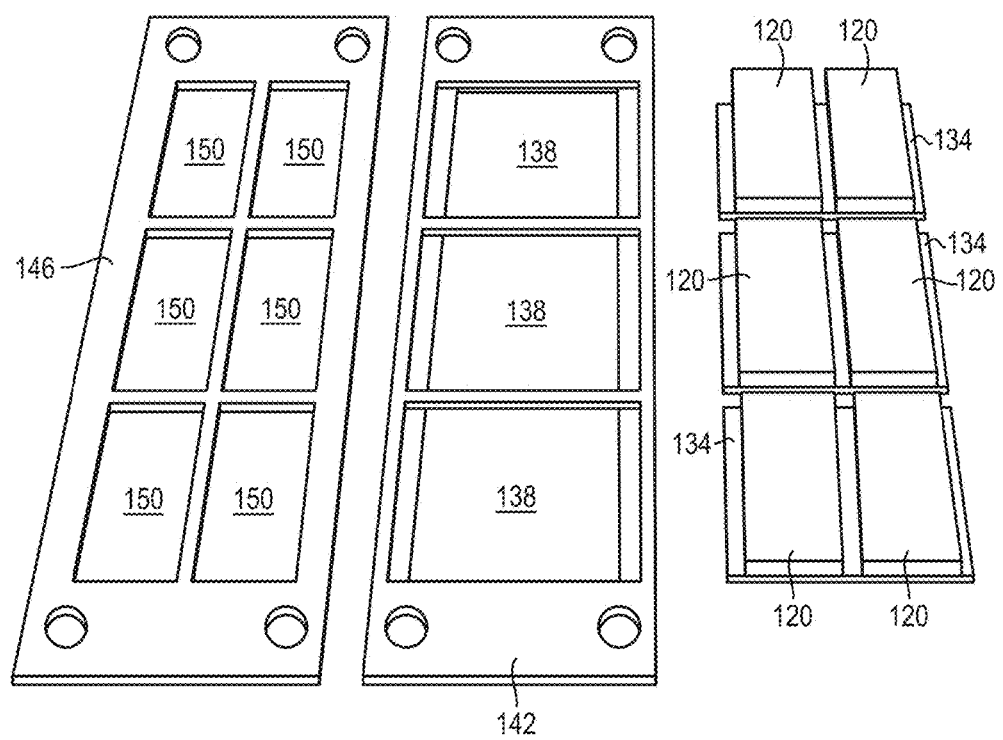
FIG. 11 is a block diagram of an embodiment of a six magnet magnetic assembly with steel back plates and aluminum supports.
Figure 12:
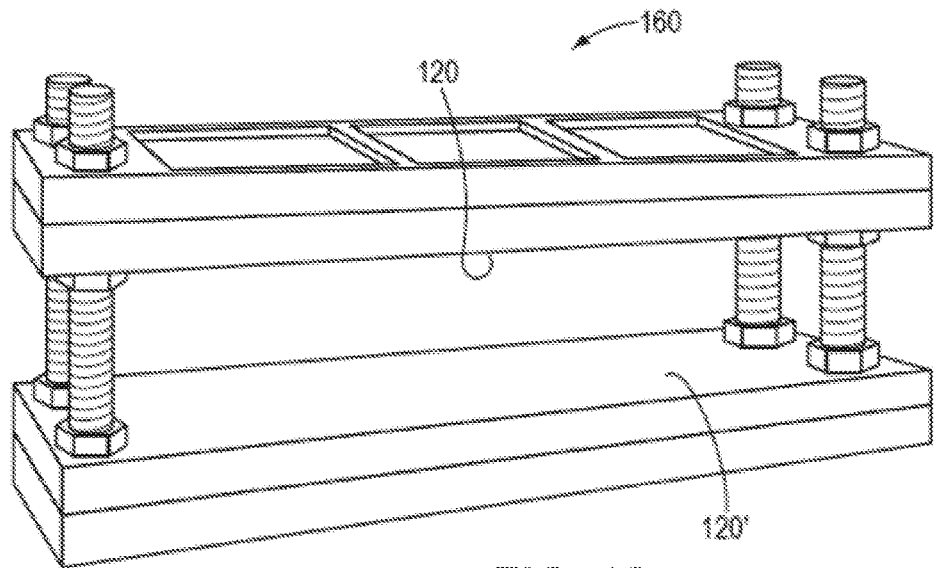
FIG. 12 is a perspective diagram of an embodiment of upper and lower magnetic assemblies that function as magnets for the invention.

Because of the cost and difficulty in producing and handling large magnets, and in order to obtain an advantageous magnetic circuit design, in one embodiment (FIG. 11), a plurality of smaller magnets 120 are grouped together before placement on opposite sides of the container 82. In one embodiment, pairs of the magnets 120 are magnetically or otherwise attached to a steel back plate 134 which extends a small distance beyond the magnets 120. The steel back plate 134 helps to focus the magnetic field and shield the area adjacent to the filter. Steel back plate 134 then rests on a lip 138 in a first part of frame 142. The second portion of the frame 146 has a plurality of openings sized and shaped to permit the magnets 130 to protrude through the frame 146 and still be held in alignment. The first 142 and second 146 portions of the aluminum frame are bolted 160 together (FIG. 12) to form a magnet assembly that along with a second magnet assembly are the two magnets 120, 120' that are positioned on opposite surfaces of the container 82. In this way, the container 82 can be removed from between the magnet assemblies 160 and the container replaced for use with another patient.

In one embodiment, the magnets are N42 grade NdFeB (Neodymium Iron Boron) with a pull of 32.2 kg, a surface flux density of 3,000 gauss and BH max energy product of 40-43 Oe. The magnets 130 are strong enough to produce a force between a pair of the magnets of 45N at a separation of 30 mm and 200N at a separation of ten mm.

How the system is used clinically to remove detrimental materials from the blood is determined in part by the nature of the material to be removed. Materials that are non-diamagnetic in and of themselves, such as malarial infected red cells, which are intrinsically paramagnetic (due to the presence of hemozoin—the paramagnetic mineral byproduct of the parasite's metabolizing of hemoglobin), may be directly removed by passing the cells through the magnetic filter 34. Diamagnetic targets such as viruses, bacteria or other toxins may be removed by labelling those targets with non-diamagnetic entities, such as for example suitably surface-functionalized ferromagnetic or ferrimagnetic nanoparticles. The principle is, for example, to coat the magnetic nanoparticles with a suitable entity, such as an antibody or antibody fragment, or a suitable ligand, for which a corresponding antigen or receptor resides in some abundance on the surface of the target entities. Under favorable conditions and with suitably designed selective targeting, it is then possible to mix the surface-functionalized magnetic nanoparticles with the patient's blood—for example by injecting the functionalized nanoparticles into the patient's bloodstream, or into the extracorporeal loop at a position upstream from the magnetic filter 34—to thereby magnetically label the target entities, and to thereafter remove those entities by passing them through the magnetic filter 34.

In operation, a catheter is placed into a blood vessel of a patient and the Luer-type or other connector of the catheter is connected to the Luer-type connector 14 of the input conduit 25. In one embodiment, the catheter has an input lumen that is connected to the input conduit 25 of the system 10 and an output lumen that is connected to the output conduit 42 of the system 10. The input conduit 25 draws blood from the input lumen of the catheter upstream from the discharge of blood which is replaced from the output conduit 42 through the output lumen of the catheter. In another embodiment, the input conduit of the system is connected to a single lumen catheter and the output conduit is connected to a second single lumen catheter. The two catheters can then be introduced into different veins or arteries of the patient.

In more detail, the pump 22 in the input conduit 26 draws blood from the patient and passes it through the magnetic filter 34. The saline drip 62 is mixed with heparin from a syringe pump 64 and mixes with the blood flowing through the input conduit 25. Once the blood passes through the filter 34, it is pumped through the output conduit 42 back into the patient through another lumen of the catheter or another catheter in the blood vessel of the patient. An air detector 46 assures that no air bubbles are in the blood stream returning to the patient. An air bubble removal device 43 can be included to remove any bubbles from the blood stream. In one embodiment, the air bubble removal is achieved by using gas-permeable plastic tubing throughout the blood circuit.

Figure 13:
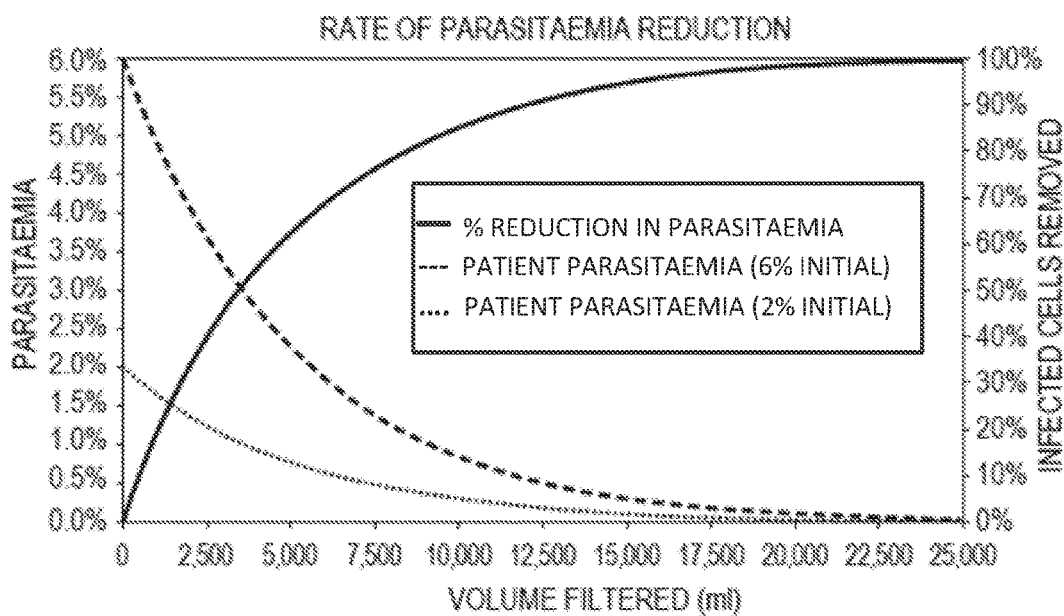
FIG. 13 is a graph showing the rate of parasite reduction with filtered volume.

FIG. 13 is a graph of a model calculation of the removal of blood cells infected with a parasite, such as malaria, from the blood as a function of total blood filtered assuming a 90% single pass efficiency, a 2% initial parasite load and a total blood volume of 5 L. As this graph shows, with this present system the bacterial, viral, parasitic, or toxic load on a patient can be removed or lowered using simple filtration. This is especially important in locations where drugs to treat the infection are difficult to obtain.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

The examples presented herein are intended to illustrate potential and specific implementations of the present disclosure. The examples are intended primarily for purposes of illustration of the invention for those skilled in the art. No particular aspect or aspects of the examples are necessarily intended to limit the scope of the present invention. The figures and descriptions of the present invention have been simplified to illustrate elements that are relevant for a clear understanding of the present invention, while eliminating, for purposes of clarity, other elements. Those of ordinary skill in the art may recognize, however, that these sorts of focused discussions would not facilitate a better understanding of the present disclosure, and therefore, a more detailed description of such elements is not provided herein.

The processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

While this disclosure contains many specifics, these should not be construed as limitations on the scope of the disclosure or of what may be claimed, but rather as descriptions of features specific to particular implementations of the disclosure. Certain features that are described in this disclosure in the context of separate implementations can also be provided in combination in a single implementation. Conversely, various features that are described in the context of a single implementation can also be provided in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described components and systems can generally be integrated together in a single product.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

Unless otherwise indicated, all numbers expressing lengths, widths, depths, or other dimensions and so forth used in the specification and claims are to be understood in all instances as indicating both the exact values as shown and as being modified by the term "about." As used herein, the term "about" refers to a ±20% variation from the nominal value. Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination. For example, any of the various components described herein and/or depicted in the figures may be combined, interchanged, or excluded from other embodiments.

What is claimed is:

1. A magnetic retention hemofilter system comprising:
a container having a first surface, a second surface, and one or more wall surfaces, the first surface, the second surface and the one or more wall surfaces defining a container volume;
an input port in fluid communication with the container;
an output port in fluid communication with the container;
a filter bed comprising a plurality of planar magnetic meshes stacked with their mesh planes in close juxtaposition and positioned within the container volume;
a first magnet positioned on a first surface of the container, the first surface substantially perpendicular to fluid flow through the container;
a first input conduit in fluid communication with the input port;
a first output conduit in fluid communication with the output port,
wherein the first magnet produces a magnetic field that is oriented substantially perpendicular relative to the planes of the planar magnetic meshes and substantially parallel to fluid flow through the container.

2. The hemofilter system of claim 1 further comprising a pump in the input conduit.

3. The hemofilter system of claim 1 further comprising a saline drip unit in fluid communication with the input conduit.

4. The hemofilter system of claim 3 wherein the saline drip unit comprises a saline reservoir and a syringe pump connected in fluid communication with the first input conduit through a T-junction.

5. The hemofilter system of claim 1 further comprising an air detector in fluid communication with the output conduit.

6. The hemofilter system of claim 1 further comprising a pressure sensor in fluid communication with the output conduit.

7. The hemofilter system of claim 1 wherein the input port is in a surface.

8. The hemofilter system of claim 1 wherein the input port is in a wall.

9. The hemofilter of claim 1 wherein fluid flow between the input and the output ports is perpendicular to the plane of the mesh.

10. The hemofilter of claim 1 wherein fluid flow between the input and the output ports is parallel to the plane of the mesh.

11. The hemofilter of claim 1 wherein fluid flow between the input and the output ports is oblique to the plane of the mesh.

12. The hemofilter of claim 1 further comprising a second magnet positioned on the second surface of the container.

13. A magnetic retention hemofilter comprising:
a container having a first surface, a second surface, and one or more wall surfaces, the first surface, the second surface and the one or more wall surfaces defining a volume;
an input port in fluid communication with the container;
an output port in fluid communication with the container;
a filter bed comprising a plurality of planar magnetic meshes with their mesh planes stacked in close juxtaposition and positioned within the container volume and coplanar with the first and second surfaces; and
a first magnet positioned on the first surface of the container, the surface substantially perpendicular to fluid flow through the container volume and the first magnet producing a magnetic field that is oriented substantially perpendicular to the planes of the planar magnetic meshes and substantially parallel to fluid flow through the container volume.

14. The hemofilter of claim 13 wherein the first magnet produces a magnetic field that is oriented substantially perpendicular to the planar magnetic meshes.

15. The hemofilter of claim 13 further comprising a second magnet positioned on the second surface of the container.

16. A magnetic retention hemofilter comprising:
a container having a first surface, a second surface, and one or more wall surfaces, the first surface, the second surface and the one or more wall surfaces defining a volume including a plurality of planar meshes creating a labyrinthine laminar flow pathway through the volume for each individual red blood cell that passes through the filter, wherein the labyrinthine laminar flow pathway is substantially perpendicular to the first surface; and
a magnet positioned on the first surface generating a magnetic field substantially perpendicular to the plurality of planar meshes and parallel to the labyrinthine laminar flow pathway through the volume,
wherein the filter is designed to produce a uniform flow characteristic at a millimeter-scale length so as to avoid dead-spots and eddies, and to maintain a sufficient rate of flow overall, and
wherein the meshes produce microvolumes adjacent to the planar meshes with a high magnetic retention force.

17. The hemofilter of claim 15 wherein the flow pathway causes a red blood cell to deviate from its unimpeded flow by more than three times the diameter of the red blood cell.

18. The hemofilter of claim 15 wherein the flow pathway causes a red blood cell to deviate from its unimpeded flow by more than about 20 microns.

19. A magnetic retention hemofilter comprising:
a first surface, a second surface, and one or more wall surfaces, the first surface, the second surface and the one or more wall surfaces defining a container volume, the first surface and the second surface oriented parallel to one another and perpendicular to the wall surfaces, the container volume comprising:
a first volume through which blood flows wherein there exists a plurality of sub-first volumes within which the blood is exposed to a magnetic field so as to produce an increased magnetic retarding force on the blood relative to the average magnetic field of the container volume; and
a second volume through which blood flows wherein there exists a plurality of sub-second volumes within which the blood experiences a lower viscoelastic drag force compared to the average drag force of the container volume;
wherein the first and second sub-volumes are substantially coincident in space,
wherein blood flow into the container volume is dispersed prior to flowing through the container volume, and
wherein blood flow through the container volume is collected prior to flowing out of the container volume.

* * * * *